(12) United States Patent
Decoster et al.

(10) Patent No.: US 6,417,145 B1
(45) Date of Patent: Jul. 9, 2002

(54) DETERGENT COSMETIC COMPOSITIONS AND USE THEREOF

(75) Inventors: Sandrine Decoster, Epinay sur Seine; Bernard Beauquey, Clichy, both of (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/591,340

(22) Filed: Jun. 9, 2000

Related U.S. Application Data

(63) Continuation of application No. 09/055,668, filed on Apr. 7, 1998, now abandoned.

(30) Foreign Application Priority Data

Apr. 7, 1997 (FR) .............................. 97 04220

(51) Int. Cl.⁷ ................................. C11D 3/37
(52) U.S. Cl. ..................................... 510/122; 510/127
(58) Field of Search ................. 510/122, 127

(56) References Cited

U.S. PATENT DOCUMENTS

| | | | |
|---|---|---|---|
| 2,258,378 A | | 10/1941 | Collman |
| 2,781,354 A | | 2/1957 | Mannheimer |
| 4,693,935 A | | 9/1987 | Mazurek |
| 4,728,571 A | | 3/1988 | Clemens et al. |
| 4,957,732 A | | 9/1990 | Grollier et al. |
| 4,972,037 A | | 11/1990 | Garbe et al. |
| 5,409,628 A | * | 4/1995 | Heinz et al. ............ 252/174.17 |
| 5,580,494 A | | 12/1996 | Sandhu et al. |
| 5,650,383 A | | 7/1997 | Dubief et al. |
| 5,693,605 A | * | 12/1997 | Isobe et al. .................. 510/499 |
| 5,747,435 A | * | 5/1998 | Patel ........................ 510/119 |
| 5,776,871 A | * | 7/1998 | Cothran et al. ............. 510/122 |
| 6,159,914 A | | 12/2000 | DeCoster et al. |
| 6,162,424 A | | 12/2000 | Decoster et al. |

FOREIGN PATENT DOCUMENTS

| | | |
|---|---|---|
| EP | 0 059 428 | 9/1982 |
| EP | 0 074 264 B1 | 3/1983 |
| EP | 0 089 749 | 9/1983 |
| EP | 0 115 252 | 8/1984 |
| EP | 0 342 834 | 11/1989 |
| EP | 0 392 320 | 10/1990 |
| EP | 0 400 976 A1 | 12/1990 |
| EP | 0 412 704 | 2/1991 |
| EP | 0 412 707 | 2/1991 |
| EP | 0 521 748 | 1/1993 |
| EP | 0 531 650 A2 | 3/1993 |
| EP | 0 582 152 | 2/1994 |
| FR | 2 589 476 | 5/1987 |
| FR | 2 641 185 | 7/1990 |
| JP | 56-72095 | 6/1981 |
| JP | 59-187095 | * 10/1984 |
| JP | 3-34914 | 2/1991 |
| JP | 4-108724 | * 4/1992 |
| JP | 6-16534 | * 1/1994 |
| JP | 06-16534 | 1/1994 |
| JP | 8176588 A | 7/1996 |
| JP | 10-203939 | 8/1998 |
| WO | 92/05234 | 4/1992 |
| WO | WO 92/05234 | * 4/1992 |
| WO | 93/08787 | 5/1993 |
| WO | 93/23009 | 11/1993 |
| WO | 93/23446 | 11/1993 |
| WO | 94/06403 | 3/1994 |
| WO | WO 94/06410 | * 3/1994 |
| WO | 94/06410 | 3/1994 |
| WO | 95/00578 | 1/1995 |
| WO | 95/01152 | 1/1995 |
| WO | 95/03776 | 2/1995 |
| WO | 95/23579 | 9/1995 |
| WO | 96/17916 | 6/1996 |
| WO | 96/32919 | 10/1996 |
| WO | 97/16168 | 5/1997 |
| WO | 98/03155 | 1/1998 |

OTHER PUBLICATIONS

English Language Derwent Abstract of EP 0 115 252.
English Language Derwent Abstract of FR 2 589 476.
English Language Derwent Abstract of FR 2 641 185.

* cited by examiner

*Primary Examiner*—John Hardee
(74) *Attorney, Agent, or Firm*—Finnegan, Henderson, Farabow, Garrett & Dunner, L.L.P.

(57) ABSTRACT

Novel detergent and conditioning compositions comprising, in a cosmetically acceptable medium, (A) a washing base comprising at least one anionic surfactant of alkyl ether sulphate type and (B) a conditioning system comprising at least one insoluble non-amino silicone and at least one cationic polymer preferably selected from diallyldimethylammonium homopolymers, and uses thereof.

48 Claims, No Drawings

DETERGENT COSMETIC COMPOSITIONS AND USE THEREOF

This is a continuation of application Ser. No. 09/055,668, filed Apr. 7, 1998, now abandoned, which is incorporated herein by reference.

Applicants reference herein the patent applications of SANDRINE DECOSTER and BERNARD BEAUQUEY for COSMETIC COMPOSITIONS CONTAINING A CATIONIC POLYMER OF LOW MOLECULAR MASS AND A SILICONE, AND USES THEREOF Ser. No. 09/055,760 DETERGENT COSMETIC COMPOSITIONS AND USE THEREOF Ser. No. 09/055,666, filed on even date herewith and incorporate the disclosure thereof specifically by reference herein.

The present invention relates to novel cosmetic compositions with improved properties, intended both for cleaning and conditioning keratin substances such as the hair and the skin, and comprising, in a cosmetically acceptable vehicle, a washing base comprising alkyl ether sulphate surfactants with detergent power, in which cationic polymers selected from homopolymers of the diallyldimethylammonium family in combination with non-amino silicones are also present as conditioners. The invention also relates to the use of the compositions in the abovementioned cosmetic application.

It is common to use detergent compositions (shampoos or shower-gels) based essentially on standard surfactants of anionic, nonionic and/or amphoteric type in particular, but more particularly of anionic type, to clean and/or wash the hair and/or the skin. These compositions are applied to wet hair and the lather generated by massaging or rubbing with the hands removes, after rinsing with water, the various types of soiling which are initially present on the hair.

Admittedly these base compositions are of good washing power, but the intrinsic cosmetic properties associated with them nevertheless remain fairly poor, owing in particular to the fact that the relatively aggressive nature of such a cleaning treatment can, in the long run, lead to more or less pronounced damage to the hair fiber, this damage being associated in particular with the gradual removal of the lipids or proteins contained in or on the surface of this fiber.

Thus, in order to improve the cosmetic properties of the above detergent compositions, and more particularly those which are to be applied to sensitized hair (i.e. hair which has been damaged or made brittle, in particular under the chemical action of atmospheric agents and/or hair treatments such as permanent-waving, dyeing or bleaching), it is now common to introduce additional cosmetic agents known as conditioners into these compositions, these conditioners being intended mainly to repair or limit the harmful or undesirable effects induced by the various treatments or aggressions to which the hair fibers are subjected more or less repeatedly. These conditioners may, of course, also improve the cosmetic behaviour of natural hair.

The conditioners most commonly used to date in shampoos are cationic polymers, silicones and/or silicone derivatives, which give washed, dry or wet hair an ease-of disentangling, softness and smoothness which are markedly better than that which can be obtained with corresponding cleaning compositions from which they are absent. In addition, on sensitized hair, it is known to use, preferably, a mixture of silicone and cationic polymer.

However, despite the progress made recently in the field of shampoos based on silicones and cationic polymers, these shampoos are not really completely satisfactory, and as such a strong need still exists currently as regards being able to provide novel products which give better performance with respect to one or more of the cosmetic properties mentioned above.

Thus, after considerable research conducted in this matter, the inventors have now found, entirely surprisingly and unexpectedly, that by using a specific and suitably selected silicone, as defined above, in detergent compositions containing specific cationic polymers as conditioners, it is possible to substantially and significantly improve the cosmetic properties associated with these compositions, while at the same time retaining their good intrinsic washing power.

The compositions in accordance with the invention give hair, after rinsing, a noteworthy treating effect which is manifested in particular by an ease of disentangling, as well as giving the hair volume and making it light, smooth, soft and supple.

Thus, according to the present invention, novel detergent conditioning compositions are now proposed, comprising, in a cosmetically acceptable medium, (A) a washing base comprising at least one anionic surfactant of alkyl ether sulphate type and (B) a conditioning system comprising at least one insoluble non-amino silicone and at least one cationic polymer selected from homopolymers containing, as main constituents of the chain, units corresponding to formula (I) or (I'):

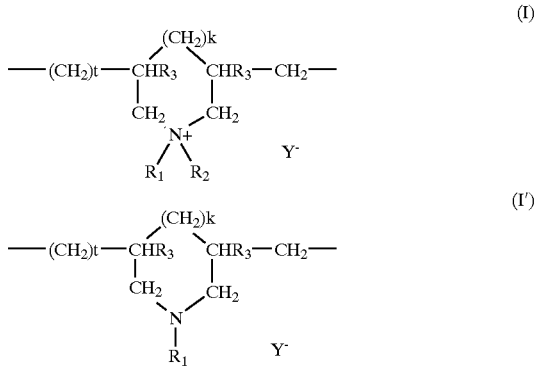

in which:
- k and t are equal to 0 or 1, the sum k+t being equal to 1;
- $R_3$ independently denotes a hydrogen atom or a methyl radical;
- $R_1$ and $R_2$ independently denote an alkyl group having from 1 to 22 carbon atoms, a hydroxyalkyl group in which the alkyl group preferably has 1 to 5 carbon atoms, a lower (1 to 5 carbon atoms) amido alkyl group, or $R_1$ and $R_2$ can denote, together with the nitrogen atom to which they are attached, heterocyclic groups such as piperidyl or morpholinyl;
- $Y^-$ is an anion such as bromide, chloride, acetate, borate, citrate, tartrate, bisulphate, bisulphite, sulphate or phosphate.

The subject of the invention is also the cosmetic use of the above compositions for cleaning and/or conditioning keratin substances such as the hair and the skin.

However, other characteristics, aspects and advantages of the invention will emerge even more clearly on reading the description which follows, as well as the concrete, but in no way limiting, examples intended to illustrate it.

A-washing Base

The compositions in accordance with the invention necessarily comprise a washing base, which is generally aqueous, comprising at least one or more anionic surfactants of alkyl ether sulphate type.

The minimum amount of washing base is that which is just sufficient to give the final composition a satisfactory foaming power and/or detergent power, and excessive amounts of washing base do not really afford additional advantages.

Thus, according to the invention, the washing base can represent preferably from 2% to 50% by weight, more preferably from 1.0% to 35% by weight and even more preferably from 12% to 25% by weight, of the total weight of the final composition.

The anionic surfactants of alkyl ether sulphate type which can preferably be used, alone or as mixtures, in the context of the present invention are salts (in particular alkaline salts, especially sodium salts, ammonium salts, amine salts, amino alcohol salts or magnesium salts) of alkyl ether sulphates, alkylamido ether sulphates, alkylaryl ether sulphates or alkyl ether sulphosuccinates, the alkyl radical of all these various compounds preferably containing from 8 to 24 carbon atoms, and the aryl radical preferably denoting a phenyl or benzyl group.

The average number of ethylene oxide or propylene oxide groups can range in particular from 2 to 50 and more particularly from 2 to 10.

Among these anionic surfactants, $C_8$–$C_{14}$ and more particularly $C_{12}$–$C_{14}$ alkyl ether sulphate salts are preferably used. These salts comprise in particular from 2 to 5 ethylene oxide groups.

The anionic surfactants are generally present in a proportion preferably of from 1 to 50% by weight, more preferably from 5 to 20% by weight, relative to the total weight of the composition.

In the compositions in accordance with the invention, mixtures of surfactants are preferably used, in particular mixtures of anionic surfactants or mixtures of anionic surfactants and of amphoteric or nonionic surfactants. A mixture which is particularly preferred is a mixture comprising at least one anionic surfactant and at least one amphoteric surfactant.

The nonionic surfactants are compounds that are well known per se (see in particular in this respect "Handbook of Surfactants" by M. R Porter, published by Blackie & Son (Glasgow and London), 1991, pp. 116–178), the disclosure of which is specifically incorporated by reference herein, and, in the context of the present invention, their nature is not a critical feature. Thus, they can be selected in particular from (non-limiting list) polyethoxylated, polypropoxylated or polyglycerolated fatty acids, alkylphenols, α-diols or alcohols having a fatty chain containing, for example, 8 to 18 carbon atoms, it being possible for the number of ethylene oxide or propylene oxide groups to range in particular from 2 to 50 and for the number of glycerol groups to range in particular from 2 to 30. Mention may also be made of copolymers of ethylene oxide and of propylene oxide, condensates of ethylene oxide and of propylene oxide with fatty alcohols; polyethoxylated fatty amides preferably having from 2 to 30 mol of ethylene oxide, polyglycerolated fatty amides containing on average 1 to 5, and in particular 1.5 to 4, glycerol groups; polyethoxylated fatty amines preferably having 2 to 30 mol of ethylene oxide; oxyethylenated fatty acid esters of sorbitan having from 2 to 30 mol of ethylene oxide; fatty acid esters of sucrose, fatty acid esters of polyethylene glycol, alkylpolyglycosides, N-alkylglucamine derivatives, amine oxides such as ($C_{10}$–$C_{14}$)alkylamine oxides or N-acylaminopropylmorpholine oxides. It will be noted that the alkylpolyglycosides constitute nonionic surfactants that are particularly suitable in the context of the present invention.

The amphoteric surfactants, whose nature is not a critical feature in the context of the present invention, can be, in particular (non-limiting list), aliphatic secondary or tertiary amine derivatives in which the aliphatic radical is a linear or branched chain containing 8 to 22 carbon atoms and containing at least one water-soluble anionic group (for example carboxylate, sulphonate, sulphate, phosphate or phosphonate); mention may also be made of ($C_8$–$C_{20}$) alkylbetaines, sulphobetaines, ($C_8$–$C_{20}$)alkylamido(C—C) alkylbetaines or ($C_8$–$C_{20}$)alkylamido($C_1$–$C_6$) alkylsulphobetaines.

Among the amine derivatives, mention may be made of the products sold under the name MIRANOL, as described in U.S. Pat. Nos. 2,528,378 and 2,781,354, the disclosures of which are specifically incorporated by reference herein, and having the structures:

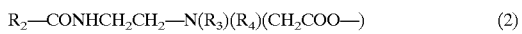

$$R_2\text{—CONHCH}_2\text{CH}_2\text{—N}(R_3)(R_4)(\text{CH}_2\text{COO—}) \quad (2)$$

in which:

$R_2$ denotes an alkyl radical derived from an acid $R_2$—COOH present in hydrolysed coconut oil, a heptyl, nonyl or undecyl radical, $R_3$ denotes a β-hydroxyethyl group and $R_4$ denotes a carboxymethyl group;

and

$$R_5\text{—CONHCH}_2\text{CH}_2\text{—N(B)(C)} \quad (3)$$

in which:

B represents —$CH_2CH_2OX'$, C represents —$(CH_2)_z$—Y', wherein z=1 or 2,

X' denotes the —$CH_2CH_2$—COOH group or a hydrogen atom,

Y' denotes —COOH or the —$CH_2$—CHOH—$SO_3H$ radical, $R_5$ denotes an alkyl radical of an acid $R_9$—COOH present in coconut oil or in hydrolysed linseed oil wherein $R_9$ denotes a $C_7$–$C_{21}$ alkyl, an alkyl radical, in particular a $C_7$, $C_9$, $C_{11}$ or $C_{13}$ alkyl radical, a $C_{17}$ alkyl radical and its iso form, an unsaturated $C_{17}$ radical.

These compounds are classified in the CTFA dictionary, 5th edition, 1993, under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, disodium capryloamphodipropionate, lauroamphodipropionic acid, cocoamphodipropionic acid.

By way of example, mention may be made of the cocoamphodiacetate sold under the tradename MIRANOL $C_2M$ concentrate by the company Rhône-Poulenc.

The nonionic or amphoteric surfactants are preferably present in a proportion of from 1 to 50% by weight, more preferably from 2 to 20% by weight, relative to the total weight of the composition.

Cationic surfactants can also be used, among which mention may be made in particular (non-limiting list) of: optionally polyoxyalkylenated, primary, secondary or tertiary fatty amine salts; quaternary ammonium salts such as tetraalkylammonium, alkylamidoalkyltrialkylammonium, trialkylbenzylammonium, trialkylhydroxyalkylammonium or alkylpyridinium chlorides or bromides; imidazoline derivatives; or amine oxides of cationic nature.

It will be noted that the cationic surfactants, whose use is not excluded, do not constitute preferred detergent surfactants for carrying out the present invention.

An anionic surfactant selected from ($C_{12}$–$C_{14}$)alkyl ether sulphates of sodium, of triethanolamine or of ammonium which are oxyethylenated with about 2.2 mol of ethylene oxide, and mixtures thereof with:
either an amphoteric surfactant such as the amine derivatives known as disodium cocoamphodipropionate or sodium cocoamphopropionate, sold in particular by the company Rhône-Poulenc under the tradename "MIRANOL C2M Conc." as an aqueous solution containing 38% active material, or under the name MIRANOL C32;
or an amphoteric surfactant of zwitterionic type, such as alkylbetaines, in particular the cocoylbetaine sold under the name "DEHYTON AB 30" as an aqueous solution containing 32% A.M. by the company Henkel; are preferably used.

B) Conditioning System
(i) Cationic Polymer(s)

For the purposes of the present invention, the expression "cationic polymer" denotes any polymer containing cationic groups and/or groups that are ionizable into cationic groups.

The compositions in accordance with the invention also necessarily comprise a cationic polymer selected from homopolymers containing, as main constituent of the chain, units corresponding to formula (I) and/or (I'):

$$—(CH_2)t—CHR_3\underset{CH_2}{\overset{(CH_2)k}{\diagup\diagdown}}CHR_3—CH_2—$$
$$\underset{R_1\quad R_2}{\overset{N+}{\diagup\diagdown}}\quad Y^-$$ (I)

$$—(CH_2)t—CHR_3\underset{CH_2}{\overset{(CH_2)k}{\diagup\diagdown}}CHR_3—CH_2—$$
$$\underset{R_1}{\overset{N}{|}}\quad Y^-$$ (I')

in which:
k and t are equal to 0 or 1, the sum k+t being equal to 1;
$R_3$ independently denotes a hydrogen atom or a methyl radical;
$R_1$ and $R_2$ independently denote an alkyl group having from 1 to 22 carbon atoms, a hydroxyalkyl group in which the alkyl group preferably has 1 to 5 carbon atoms, a lower (1 to 5 carbon atoms) amido alkyl group, or $R_1$ and $R_2$ can denote, together with the nitrogen atom to which they are attached, heterocyclic groups such as piperidyl or morpholinyl;
$Y^-$ is an anion such as bromide, chloride, acetate, borate, citrate, tartrate, bisulphate, bisulphite, sulphate or phosphate.

These polymers are described in particular in French patent 2,080,759, in its Certificate of Addition 2,190,406, the disclosures of which are specifically incorporated by reference herein or in U.S. Pat. Nos. 3,996,146 and 3,288,770, the disclosures of which are specifically incorporated by reference herein.

Preferably, $R_1$ and $R_2$ independently denote methyl or ethyl and $R_3$ denotes a hydrogen atom.

The cationic polymers used generally have a weight-average molecular a mass preferably ranging from approximately 500 to approximately $5\times10^6$ and more preferably from approximately $10^3$ to approximately $5\times10^5$.

Preferably, cationic polymers according to the invention have a cationic charge density greater than or equal to about 5 meq./gram and more preferably from 5 to 10 meq./gram. The cationic charge represents the number of cationic charge per gram of polymer.

Among the polymers defined above, mention may be made more particularly of diallyidimethylammonium chloride homopolymers such as the one sold under the name "MERQUAT® 100" by the company Calgon.

According to the invention, the cationic polymer(s) can represent preferably from 0.001% to 10% by weight, more preferably from 0.005% to 5% by weight and even more preferably from 0.01% to 3% by weight, of the total weight of the final composition.

(ii) Insoluble Silicones

According to an essential characteristic of the detergent compositions in accordance with the invention, these compositions also contain at least one insoluble non-amino silicone.

Hereinabove and hereinbelow, in accordance with the definition generally accepted, the term silicone or polysiloxane is understood to denote any organosilicon polymer or oligomer with a linear or cyclic, branched or crosslinked structure, of variable molecular weight, obtained by polymerization and/or polycondensation of suitably functionalized silanes, and including a repetition of main units in which the silicon atoms are connected together by oxygen atoms (siloxane bond $\equiv Si—O—Si\equiv$), optionally substituted hydrocarbon radicals being linked directly via a carbon atom to the said silicon atoms. The most common hydrocarbon radicals are alkyl radicals, especially $C_1$–$C_{10}$ alkyl radicals and in particular methyl, fluoroalkyl radicals, aryl radicals and in particular phenyl, and alkenyl radicals and in particular vinyl; other types of radicals which can be linked, either directly or via a hydrocarbon radical, to the siloxane chain are, in particular, hydrogen, halogens and in particular chlorine, bromine or fluorine, thiols, alkoxy radicals, polyoxyalkylene (or polyether) radicals and in particular polyoxyethylene and/or polyoxypropylene, hydroxyl or hydroxyalkyl radicals, amide groups, acyloxy or acyloxyalkyl radicals, anionic groups such as carboxylates, thioglycolates, sulphosuccinates, thiosulphates, phosphates and sulphates, this list obviously being in no way limiting (so-called "organomodified" silicones).

According to the invention, the term non-amino silicone denotes any silicone not containing at least one primary, secondary or tertiary amine or a quaternary ammonium group.

The silicones which can be used in accordance with the invention are, in particular, polyorganosiloxanes which can be in the form of oils, waxes, resins or gums.

The organopolysiloxanes are defined in greater detail in the book by Walter Noll "Chemistry and Technology of Silicones" (1968) Academic Press, the disclosure of which is specifically incorporated by reference herein. They can be volatile or non-volatile.

When they are volatile, the silicones are more particularly selected from those having a boiling point ranging from 60° C. to 260° C., and even more particularly from:
(i) cyclic silicones preferably containing from 3 to 7 and more preferably from 4 to 5 silicon atoms. These are, for example, octamethylcyclotetrasiloxane sold in particular under the name "VOLATILE SILICONE 7207" by Union Carbide or "SILBIONE® 70045 V 2" by Rhône-Poulenc, decamethylcyclopentasiloxane sold under the name "VOLATILE SILICONE 7158" by Union Carbide, and "SILBIONE® 70045 V 5" by Rhône-Poulenc, and mixtures thereof.

Mention may also be made of cyclocopolymers of the dimethylsiloxane/methylalkylsiloxane type, such as "VOLATILE SILICONE FZ 3109" sold by the company Union Carbide, of chemical structure:

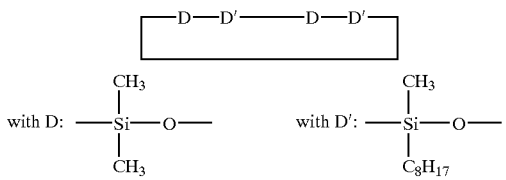

Mention may also be made of mixtures of cyclic silicones with organosilicon compounds, such as the mixture of octamethylcyclotetrasiloxane and tetratrimethylsilylpentaerythritol (50/50) and the mixture of octamethylcyclotetrasiloxane and oxy-1,1'-bis(2,2,2',2',3,3'-hexatrimethylsilyloxy)neopentane;

(ii) linear volatile silicones having 2 to 9 silicon atoms and having a viscosity of less than or equal to $5 \times 10^{-6}$ m$^2$/s at 25° C. This is, for example, decamethyltetrasiloxane sold in particular under the name "SH 200®" by the company Toray Silicone. Silicones forming part of this category are also described in the article published in Cosmetics and Toiletries, Vol. 91, January 1976, pp. 27–32, Todd & Byers "Volatile Silicone Fluids for Cosmetics," the disclosure of which is specifically incorporated by reference herein.

Non-volatile silicones, and more particularly polyalkylsiloxanes, polyarylsiloxanes, polyalkylarylsiloxanes, silicone gums and resins, polyorganosiloxanes modified with organofunctional groups, and mixtures thereof, are preferably used.

These silicones are more particularly selected from polyalkylsiloxanes, among which mention may be made mainly of polydimethylsiloxanes containing trimethylsilyl end groups having a viscosity preferably of from $5 \times 10^{-6}$ to 2.5 m$^2$/s at 25° C. and more preferably $1 \times 10^{-5}$ to 1 m$^2$/s.

Among these polyalkylsiloxanes, mention may be made, in a non-limiting manner, of the following commercial products:

the SILBIONE® oils of the series 47 and 70 047 or the MIRASIL® oils sold by Rhône-Poulenc, such as, for example, the oil 70 047 V 500 000;

the oils of the MIRASIL® series sold by the company Rhône-Poulenc;

the oils of the 200 series from the company Dow Corning;

the VISCASIL® oils from General Electric and certain oils of the SF series (SF 96, SF 18) from General Electric.

Mention may also be made of polydimethylsiloxanes containing dimethylsilanol end groups (Dimethiconol according to the CTFA name) such as the oils of the 48 series from the company Rhône-Poulenc.

In this category of polyalkylsiloxanes, mention may also be made of the products sold under the names "ABIL® Wax 9800 and 9801" by the company Goldschmidt, which are poly(C$_1$–C$_{20}$)alkylsiloxanes.

The polyalkylarylsiloxanes are selected particularly from linear and/or branched polydimethyl methylphenylsiloxanes and polydimethyl diphenylsiloxanes with a viscosity of from $1 \times 10^{-5}$ to $5 \times 10^2$ m$^2$/s is at 25° C.

Among these polyalkylarylsiloxanes, mention may be made, by way of example, of the products sold under the following names:

the SILBIONE® oils of the 70 641 series from Rhône-Poulenc;

the oils of the RHODORSIL 70 633 and 763 series from Rhône-Poulenc;

the oil DOW CORNING 556® Cosmetic Grade Fluid from Dow Corning;

the silicones of the PK series from Bayer, such as the product PK20;

the silicones of the PN and PH series from Bayer, such as the products PN1000 and PH1000;

certain oils of the SF series from General Electric, such as SF 1023, SF 1154, SF 1250 and SF 1265.

The silicone gums which can be used in accordance with the invention are, in particular, polydiorganosiloxanes having high weight-average molecular weights ranging from 200 000 to 3 000 000, used alone or as a mixture in a solvent. This solvent can be selected from volatile silicones, polydimethylsiloxane (PDMS) oils, polyphenylmethylsiloxane (PPMS) oils, isoparaffins, polyisobutylenes, methylene chloride, pentane, dodecane and tridecane, or mixtures thereof.

Mention may be made more particularly of the following products:

polydimethylsiloxane
polydimethylsiloxane/methylvinylsiloxane gums,
polydimethylsiloxane/diphenylmethylsiloxane,
polydimethylsiloxane/phenylmethylsiloxane,
polydimethylsiloxane/diphenylsiloxane/methylvinylsiloxane.

Products which can be used more particularly in accordance with the invention are mixtures such as:

mixtures formed from a polydimethylsiloxane hydroxylated at the end of the chain (referred to as dimethiconol according to the nomenclature in the CTFA dictionary) and of a cyclic polydimethylsiloxane (referred to as cyclomethicone according to the nomenclature in the CTFA dictionary), such as the product Q2 1401 sold by the company Dow Corning;

mixtures formed from a polydimethylsiloxane gum with a cyclic silicone, such as the product SF 1214 SILICONE FLUID from the company General Electric; this product is an SF 30 gum corresponding to a dimethicone, having a molecular weight of 500 000, dissolved in SF 1202 SILICONE FLUID oil corresponding to decamethylcyclopentasiloxane;

mixtures of two PDMSs of different viscosities, and more particularly of a PDMS gum and a PDMS oil, such as the product SF 1236 from the company General Electric. The product SF 1236 is a mixture of a gum SE 30 defined above, having a viscosity of 20 m$^2$/s, and an oil SF 96, with a viscosity of $5 \times 10^{-6}$ m$^2$/s. This product preferably contains 15% Sx 30 gum and 85% SF 96 oil.

The organopolysiloxane resins which can be used in accordance with the invention are crosslinked siloxane systems containing the following units: R$_2$SiO$_{2/2}$, R$_3$SiO$_{1/2}$, RSiO$_{3/2}$, and SiO$_{4/2}$, in which R represents a hydrocarbon group having from 1 to 16 carbon atoms or a phenyl group. Among these products, those particularly preferred are the ones in which R denotes a C$_1$–C$_4$ lower alkyl radical, more particularly methyl, or a phenyl radical.

Among these resins, mention may be made of the product sold under the name "DOW CORNING 593" or those sold under the names "SILICONE FLUID SS 4230 and SS 4267" by the company General Electric, and which are silicones of dimethyl/trimethyl siloxane structure.

Mention may also be made of the resins of the trimethylsiloxysilicate type sold in particular under the names X22-4914, X21-5034 and X21-5037 by the company Shin-Etsu.

The organomodified silicones which can be used in accordance with the invention are silicones as defined above and containing in their structure one or more organofunctional groups attached via a hydrocarbon radical.

Among the organomodified silicones, mention may be made of polyorganosiloxanes containing:

polyethylenoxy and/or polypropylenoxy groups optionally containing $C_6$–$C_{24}$alkyl groups, such as the products known as dimethicone copolyol sold by the company Dow Corning under the name DC 1248 or the oils Silwet L 722, L 7500, L 77 and L 711 from the company Union Carbide and the ($C_{12}$)alkylmethicone copolyol sold by the company Dow Corning under the name Q2 5200;

thiol groups such as the products sold under the names "GP 72 A" and "GP 71" from Genesee;

alkoxy groups such as the product sold under the name "SILICONE COPOLYMER F-755" by SWS Silicones and ABIL WAX 2428, 2434 and 2440 by the company Goldschmidt;

anionic groups of the carboxylic type, such as, for example, in the products described in patent EP 186,507 from the company Chisso Corporation, or of the alkylcarboxylic type, such as those present in the product X-22-3701E from the company Shin-Etsu; 2-hydroxyalkyl sulphonate; 2-hydroxyalkyl thiosulphate, such as the products sold by the company Goldschmidt under the names "ABIL S201" and "ABIL S255".

According to the invention, silicones comprising a polysiloxane portion and a non-silicone organic chain portion, one of the two portions constituting the main chain of the polymer and the other being grafted onto the said main chain, can also be used. These polymers are described, for example, in patent applications EP-A-412,704, EP-A-412,707, EP-A-640,105 and WO 95/00578, EP-A-582,152 and WO 93/23009 and U.S. Pat. Nos. 4,693,935, 4,728,571 and 4,972,037, the disclosures of which are specifically incorporated by reference herein. These polymers are preferably anionic or nonionic.

Such polymers are, for example, copolymers which may be obtained by radical polymerization from a monomer mixture comprising:

a) 50 to 90% by weight of tert-butyl acrylate;
b) 0 to 40% by weight of acrylic acid;
c) 5 to 40% by weight of silicone macromer of formula:

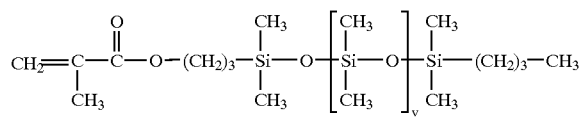

in which:

V is a number ranging from 5 to 700; the weight percentages being calculated relative to the total weight of the monomers.

Other examples of grafted silicone polymers are, in particular, polydimethylsiloxanes (PDMSs) onto which are grafted, via a connecting chain of thiopropylene type, mixed polymer units of the poly(meth)acrylic acid type and of the polyalkyl (meth)acrylate type and polydimethylsiloxanes (PDMSs) onto which are grafted, via a connecting chain of thiopropylene type, polymer units of the polyisobutyl (meth) acrylate type.

According to the invention, all of the silicones can also be used in the form of emulsions.

The polyorganosiloxanes which are particularly preferred in accordance with the invention are:

non-volatile silicones selected from the family of polyalkylsiloxanes containing trimethylsilyl end groups, such as the polydimethylsiloxane oils having a viscosity ranging from 0.2 to 2.5 $m^2$/s at 25° C. from the SILBIONE 70047 and 47 series and more particularly the oil 70 047 V 500 000, which is sold by the company Rhône-Poulenc, polyalkylsiloxanes containing dimethylsilanol end groups or polyalkylarylsiloxanes such as the SILBIONE oil 70641 V 200 sold by the company Rhône-Poulenc.

The cosmetic compositions in accordance with the invention contain the non-amino silicones defined above in weight contents which can preferably range from 0.05% to 10%, more preferably from 0.1% to 5% and even more preferably from 0.2% to 3%, relative to the total weight of the composition.

The cosmetically acceptable aqueous medium can comprise water or a mixture of water and a cosmetically acceptable solvent such as a $C_1$–$C_4$ lower alcohol, for instance ethanol, isopropanol, tert-butanol or n-butanol; alkylene glycols such as propylene glycol and glycol ethers.

The detergent compositions according to the invention have a final pH generally ranging from 3 to 10. More preferably, this pH ranges from 5 to 8. The pH can be adjusted to the desired value conventionally by adding a base (organic or inorganic) into the composition, for example aqueous ammonia or a primary, secondary or tertiary (poly)amine such as monoethanolamine, diethanolamine, triethanolamine, isopropanolamine or 1,3-propanediamine, or alternatively by adding an acid, preferably a carboxylic acid such as, for example, citric acid.

The compositions in accordance with the invention can contain, in addition to the combination defined above, viscosity modifiers such as electrolytes, or thickeners. Mention may be made in particular of sodium chloride, sodium xylenesulphonate, scleroglucans, xanthan gums, fatty acid alkanolamides, alkanolamides of carboxylic acid alkyl ether optionally oxyethylenated with up to mol of ethylene oxide, such as the product sold under the name "AMINOL A15" by the company Chem Y, crosslinked polyacrylic acids and crosslinked acrylic acid/$C_{10}$–$C_{30}$ alkyl acrylate copolymers. These viscosity modifiers are used in the a compositions according to the invention in proportions which may preferably range up to 10% by weight relative to the total weight of the composition.

The compositions in accordance with the invention can also contain up to 5% of pearlescent agents or opacifiers that are well known in the state of the art, such as, for example, sodium or magnesium palmitate, sodium or magnesium stearate or hydroxystearate, acyl derivatives containing a fatty chain, such as monostearates or distearates of ethylene glycol or of polyethylene glycol, fatty-chain ethers such as distearyl ether or 1-hexadecyloxyoctadodecanol.

The compositions in accordance with the invention can optionally also contain other agents whose effect is to improve the cosmetic properties of keratin substances. Mention may be made, in this respect, of cationic surfactants, anionic, nonionic, cationic or amphoteric polymers, proteins, proteinhydrolysates, ceramides, pseudoceramides, fatty acids with linear or branched $C_{16}$–$C_{40}$ chains, such as 18-methyleicosanoic acid, hydroxy acids, vitamins, panthenol and water-soluble or liposoluble sunscreens, and mixtures thereof.

Needless to say, a person skilled in the art will take care to select this or these optional complementary compounds and/or the amounts thereof such that the advantageous properties intrinsically associated with the combination (washing base+specific cationic polymer+non-amino silicone) in accordance with the invention are not, or are not substantially, adversely affected by the addition(s) envisaged.

These compositions can be in the form of relatively thickened liquids, creams or gels and they are mainly suitable for washing and caring for keratin substances such as the skin or the hair.

The compositions according to the invention are preferably used as shampoos for washing and conditioning the hair, and they are applied, in this respect, to wet hair in amounts that are effective to wash them, this application being followed by rinsing with water.

The compositions in accordance with the invention can also be used as shower gels for washing and conditioning the hair and the skin, in which case they are applied to wet hair or skin and are rinsed after application.

The subject of the invention is also the cosmetic use of the above compositions for cleansing and conditioning keratin substances such as the hair and the skin.

The compositions can, for example, be used for removing make-up from keratin substances such as the skin (for example the face, the neck or the lips), the eyelashes or the eyebrows.

The subject of the invention is also a process for washing and conditioning keratin substances such as the hair, which involves applying an effective amount of a composition as defined above to the said wet substances, and then in rinsing with water after optionally leaving the composition on the keratin substances for a while.

Concrete, but in no way limiting, examples illustrating the invention will now be given.

EXAMPLE 1

Two shampoo compositions, one in accordance with the invention (composition A) and the other a comparative composition (composition B), were prepared:

|  | A Invention | B Comparative |
|---|---|---|
| Sodium lauryl ether sulphate (70/30 $C_{12}/C_{14}$) containing 2.2 mol of ethylene oxide, as an aqueous solution containing 70% A.M. (A.M. = active material) | 15.5 g A.M. | 15.5 g A.M. |
| Cocobetaine containing 32% A.M. (*) | 2.9 g A.M. | 2.9 g A.M. |
| Cationic polymer (**) | 0.6 g | — |
| Cationic polymer (****) | — | 0.6 g |
| Insoluble non-amino silicone (***) | 2 g | 2 g |
| Sodium cetostearyl sulphate | 0.75 g | 0.75 g |
| Ethylene glycol distearate | 2 g | 2 g |
| Citric acid qs pH | 5 | 5 |
| Fragrance, preserving agents | qs | qs |
| Demineralized water qs | 100 g | 100 g |

(*) DEHYTON ® AB 30 from Henkel
(**): Dimethyldiallylammonium chloride homopolymer sold under the name MERQUAT ® 100 (MW 400,000) by the company Calgon
(***): Polydimethylsiloxane sold under the name FLUID DC 200, with a viscosity of 60,000 Cst, by the company Dow Corning
(****): Quaternized cellulose sold under the name JR 400 by the company Union Carbide.

Shampooing was carried out by applying about 12 g of composition A to premoistened hair. The shampoo was worked into a lather and was then rinsed thoroughly with water.

The same procedure as above was carried out with the comparative composition B.

A panel of experts evaluated the disentangling of the wet hair, the disentangling of the dried damp hair and the softness and smoothness of the dried hair.

All the experts indicated a marked improvement in these properties for hair treated with composition A according to the invention.

EXAMPLE 2

The following shampoo composition was prepared:

| | |
|---|---|
| Sodium lauryl ether sulphate (70/30 $C_{12}/C_{14}$) containing 2.2 mol of ethylene oxide, as an aqueous solution containing 70% A.M. (A.M. = active material) | 14 g A.M. |
| Cocobetaine containing 30% A.M. (*) | 1.8 g A.M. |
| Cationic polymer (**) | 0.6 g A.M. |
| Insoluble non-amino silicone (***) | 3 g A.M. |
| Mixture of cetyl alcohol and 1-(hexadecyloxy)-2-octadecanol | 2.5 g |
| Coconut acid monoisopropanolamide | 1 g |
| Citric acid qs pH | 6 |
| Fragrance, preserving agents | qs |
| Demineralized water qs | 100 g |

(*) DEHYTON ® AB 30 from Henkel
(**): Dimethyldiallylammonium chloride homopolymer as an aqueous solution containing 40% active material sold under the name MERQUAT ® 100 (MW 400,000) by the company Calgon
(***): Polydimethylsiloxane as an aqueous emulsion containing 50% active material, sold under the name DC 2-1691 by the company Dow Corning

EXAMPLE 3

The following shampoo composition was prepared:

| | |
|---|---|
| Sodium lauryl ether sulphate (70/30 by weight $C_{12}/C_{14}$) containing 2.2 mol of ethylene oxide, as an aqueous solution containing 70% A.M. (A.M. = active material) | 14 g A.M. |
| Sodium cocoamidoethyl (N-hydroxyethyl-N-carboxymethyl)glycinate (*) | 1.8 g A.M. |
| Cationic polymer (**) | 0.6 g A.M. |
| Insoluble non-amino silicone (***) | 3 g A.M. |
| Mixture of cetyl alcohol and 1-(hexadecyloxy)-2-octadecanol | 2.5 g |
| Coconut acid monoisopropanolamide | 1 g |
| Citric acid qs pH | 7 |
| Fragrance, preserving agents | qs |
| Demineralized water qs | 100 g |

(*): CHIMEXANE HD from Chimex
(**): Dimethyldiallylammonium chloride homopolymer sold under the name MERQUAT 100 (MW 400,000) by the company Calgon, as an aqueous solution containing 40% active material
(***): Polydimethylsiloxane (viscosity 300,000 Cst) sold under the name SILICONE FLUID AK 300,000 by the company Wacker.

We claim:

1. A detergent and conditioning composition comprising, in a cosmetically acceptable medium,
    (A) a washing base comprising at least one anionic surfactant chosen from alkyl ether sulphates, alkylamido ether sulphates, alkylaryl ether sulphates, alkyl ether sulphosuccinates and salts thereof; and (B) a conditioning system comprising at least one insoluble non-amino silicone and at least one cationic polymer selected from homopolymers containing, as the main constituent of the chain, repeating units selected from formulae (I) and (I')

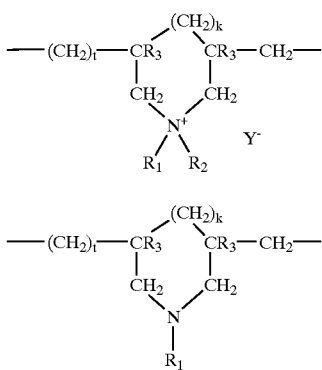

in which:
k and t are equal to 0 or 1, wherein the sum k+t equals 1;
$R_3$ independently denotes a hydrogen atom or a methyl radical;
$R_1$ and $R_2$ independently denote an alkyl group having from 1 to 22 carbon atoms, a hydroxyalkyl group in which the alkyl group has from 1 to 5 carbon atoms, a lower amido alkyl group in which the alkyl group has from 1 to 5 carbon atoms, or $R_1$ and $R_2$ can denote, together with the nitrogen atom to which they are attached, a heterocyclic group; and
$Y^-$ is an anion; and
wherein said composition is in the form of a thickened liquid, a cream or a gel;
with the proviso that said composition does not contain a protein.

2. A detergent and conditioning composition according to claim 1, wherein said heterocyclic group is selected from piperidyl and morpholinyl and wherein said anion is selected from bromide, chloride, acetate, borate, citrate, tartrate, bisulphate, bisulphite, sulphate and phosphate.

3. A detergent and conditioning composition according to claim 1, wherein the alkyl radicals of said at least one anionic surfactant contain from 8 to 24 carbon atoms, and the aryl radicals of said at least one anionic surfactant are chosen from a phenyl, an alkylaryl and an alkylarylalkyl group.

4. A detergent and conditioning composition according to claim 1, wherein said at least one alkyl ether sulphate anionic surfactant is selected from $C_8$–$C_{14}$ alkyl ether sulphate salts.

5. A detergent and conditioning composition according to claim 1, wherein said at least one alkyl ether sulphate anionic surfactant is selected from $C_{12}$–$C_{14}$ alkyl ether sulphate salts.

6. A detergent and conditioning composition according to claim 1, wherein $R_1$ and $R_2$ independently denote methyl or ethyl and R denotes a hydrogen atom.

7. A detergent and conditioning composition according to claim 1, wherein said at least one cationic polymer is selected from diallyidimethylammonium chloride homopolymers.

8. A detergent and conditioning composition according to claim 1, wherein said at least one insoluble non-amino silicone is selected from polyorganosiloxanes in the form of oils, waxes, resins or gums.

9. A detergent and conditioning composition according to claim 1, wherein said washing base is present in an amount ranging from 2 to 50% by weight relative to the total weight of said composition.

10. A detergent and conditioning composition according to claim 9, wherein said washing base is present in an amount ranging from 10 to 35% by weight relative to the total weight of said composition.

11. A detergent and conditioning composition according to claim 10, wherein said washing base is present in an amount ranging from 12 to 25% by weight relative to the total weight of said composition.

12. A detergent and conditioning composition according to claim 1, wherein said at least one alkyl ether sulphate anionic surfactant is present in an amount ranging from 1 to 50% by weight relative to the total weight of said composition.

13. A detergent and conditioning composition according to claim 12, wherein said at least one alkyl ether sulphate anionic surfactant is present in an amount ranging from 5 to 20% by weight relative to the total weight of said composition.

14. A detergent and conditioning composition according to claim 1, wherein said at least one cationic polymer is present in an amount ranging from 0.001% to 10% by weight relative to the total weight of said composition.

15. A detergent and conditioning composition according to claim 14, wherein said at least one cationic polymer is present in an amount ranging from 0.005% to 5% by weight relative to the total weight of said composition.

16. A detergent and conditioning composition according to claim 15, wherein said at least one cationic polymer is present in an amount ranging from 0.01% to 3% by weight relative to the total weight of said composition.

17. A detergent and conditioning composition according to claim 1, wherein said at least one insoluble non-amino silicone is present in an amount ranging from 0.05% to 10% by weight relative to the total weight of said composition.

18. A detergent and conditioning composition according to claim 17, wherein said at least one insoluble non-amino silicone is present in an amount ranging from 0.1% to 5% by weight relative to the total weight of said composition.

19. A detergent and conditioning composition according to claim 18, wherein said at least one insoluble non-amino silicone is present in an amount ranging from 0.2% to 3% by weight relative to the total weight of said composition.

20. A detergent and conditioning composition according to claim 1 for cleansing and/or conditioning and/or removing make-up from a keratin substance.

21. A detergent and conditioning composition according to claim 20, wherein said keratin substance is hair or skin.

22. A detergent and conditioning composition according to claim 1, wherein said cosmetically acceptable medium comprises water or water and a cosmetically acceptable solvent.

23. A detergent and conditioning composition according to claim 22, wherein said cosmetically acceptable solvent is selected from $C_1$–$C_4$ lower alcohols and alkylene glycols.

24. A detergent and conditioning composition according to claim 23, wherein said $C_1$–$C_4$ lower alcohols are selected from ethanol, isopropanol, tert-butanol, and n-butanol.

25. A detergent and conditioning composition according to claim 23, wherein said alkylene glycols are selected from propylene glycol and glycol ethers.

26. A detergent and conditioning composition according to claim 1, wherein said composition has a pH ranging from 3 to 10.

27. A detergent and conditioning composition according to claim 25, wherein said composition has a pH ranging from 5 to 8.

28. A detergent and conditioning composition according to claim 1, wherein said composition further comprises at least one additive.

29. A detergent and conditioning composition according to claim 28, wherein said at least one additive is selected from viscosity modifiers, pearlescent agents and opacifiers, and adjuvants to improve the cosmetic properties of keratin substances.

30. A prowess for washing and conditioning a keratin substance comprising:
   wetting said keratin substance,
   applying to said keratin substance an effective amount of at least one composition comprising, in a cosmetically acceptable medium,
   (A) a washing base comprising at least one anionic surfactant chosen from alkyl ether sulphates, alkylamido ether sulphates, alkylaryl ether sulphates, and alkyl ether sulphosuccinates and salts thereof; and
   (B) a conditioning system comprising at least one insoluble non-amino silicone and at least one cationic polymer selected from homopolymers containing, as the main constituent of the chain, repeating units selected from formulae (I) and (I'):

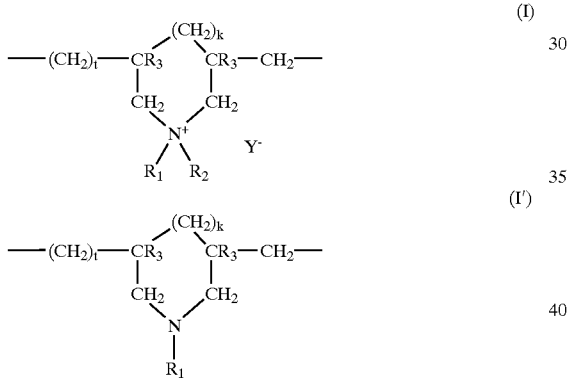

in which:
   k and t are equal to 0 or 1, wherein the sum k+t equals 1;
   $R_3$ independently denotes a hydrogen atom or a methyl radical;
   $R_1$ and $R_2$ independently denote an alkyl group having from 1 to 22 carbon atoms, a hydroxyalkyl group in which the alkyl group has from 1 to 5 carbon atoms, a lower amido alkyl group in which the alkyl group has from 1 to 5 carbon atoms, or $R_1$ and $R_2$ can denote, together with the nitrogen atom to which they are attached, a heterocyclic group; and
   $Y^-$ is an anion; and
   wherein said composition is in the form of a thickened liquid, a cream or a gel, and with the proviso that the composition does not contain a protein, optionally leaving the composition on the keratin substance for a period of time, and then rinsing said keratin substance with water.

31. A process according to claim 30, wherein said keratin substance is human hair.

32. A process according to claim 30, wherein said keratin substance is human skin.

33. A detergent and conditioning composition comprising, in a cosmetically acceptable medium,
   (A) a washing base comprising at least one anionic surfactant chosen from alkyl ether sulphates, alkylamido ether sulphates, alkylaryl ether sulphates, alkyl ether sulphosuccinates and salts thereof; and
   (B) a conditioning system comprising at least one insoluble non-amino silicone and at least one cationic polymer selected from homopolymers containing, as the main constituent of the chain, repeating units selected from formulae (I) and (I')

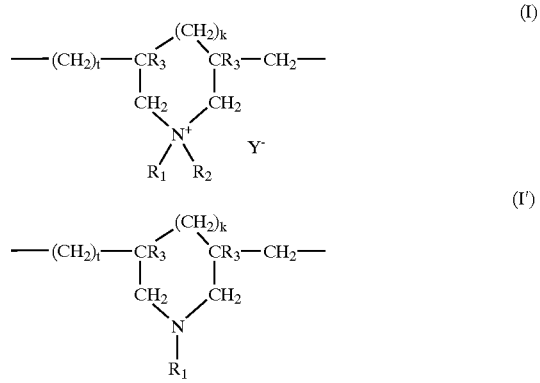

in which:
   k and t are equal to 0 or 1, wherein the sum k+t equals 1;
   $R_3$ independently denotes a hydrogen atom or a methyl radical;
   $R_1$ and $R_2$ independently denote an alkyl group having from 1 to 22 carbon atoms, a hydroxyalkyl group in which the alkyl group has from 1 to 5 carbon atoms, a lower amido alkyl group in which the alkyl group has from 1 to 5 carbon atoms, or $R_1$ and $R_2$ can denote, together with the nitrogen atom to which they are attached, a heterocyclic group; and
   $Y^-$ is an anion; and
   (C) at least one additional ingredient chosen from ethylene glycol monostearate, ethylene glycol distearate, distearyl ether, and 1-hexadecyloxyoctadodecanol.

34. A detergent and conditioning composition according to claim 33, wherein said at least one cationic polymer is selected from diallyldimethylammonium chloride homopolymers.

35. A detergent and conditioning composition according to claim 33, wherein said at least one insoluble non-amino silicone is selected from polyorganosiloxanes in the form of oils, waxes, resins, and gums.

36. A detergent and conditioning composition according to claim 33, wherein said washing base is present in an amount ranging from 2 to 50% by weight relative to the total weight of said composition.

37. A detergent and conditioning composition according to claim 36, wherein said washing base is present in an amount ranging from 10 to 35% by weight relative to the total weight of said composition.

38. A detergent and conditioning composition according to claim 37, wherein said washing base is present in an amount ranging from 12 to 25% by weight relative to the total weight of said composition.

39. A detergent and conditioning composition according to claim 33, wherein said at least one anionic surfactant is present in an amount ranging from 1 to 50% by weight relative to the total weight of said composition.

40. A detergent and conditioning composition according to claim 39, wherein said at least one anionic surfactant is present in an amount ranging from 5 to 20% by weight relative to the total weight of said composition.

41. A detergent and conditioning composition according to claim 33, wherein said at least one cationic polymer is present in an amount ranging from 0.001% to 10% by weight relative to the total weight of said composition.

42. A detergent and conditioning composition according to claim 41, wherein said at least one cationic polymer is present in an amount ranging from 0.005% to 5% by weight relative to the total weight of said composition.

43. A detergent and conditioning composition according to claim 42, wherein said at least one cationic polymer is present in an amount ranging from 0.01% to 3% by weight relative to the total weight of said composition.

44. A detergent and conditioning composition according to claim 33, wherein said at least one insoluble non-amino silicone is present in an amount ranging from 0.05% to 10% by weight relative to the total weight of said composition.

45. A detergent and conditioning composition according to claim 44, wherein said at least one insoluble non-amino silicone is present in an amount ranging from 0.1% to 5% by weight relative to the total weight of said composition.

46. A detergent and conditioning composition according to claim 45, wherein said at least one insoluble non-amino silicone is present in an amount ranging from 0.2% to 3% by weight relative to the total weight of said composition.

47. A detergent and conditioning composition according to claim 33, wherein said at least one additional ingredient is present in an amount of up to 5% by weight relative to the total weight of said composition.

48. A process for washing and conditioning a keratin substance comprising:

wetting said keratin substance, applying to said keratin substance an effective amount of at least one composition comprising, in a cosmetically acceptable medium, (A) a washing base comprising at least one anionic surfactant chosen from alkyl ether sulphates, alkylamido ether sulphates, alkylaryl ether sulphates, and alkyl ether sulphosuccinates and salts thereof; and (B) a conditioning system comprising at least one insoluble non-amino silicone and at least one cationic polymer selected from homopolymers containing, as the main constituent of the chain, repeating units selected from formulae (I) and (I'):

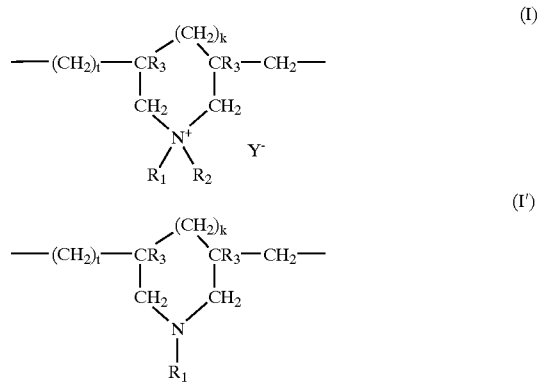

in which:

k and t are equal to 0 or 1, wherein the sum k+t equals 1;

$R_3$ independently denotes a hydrogen atom or a methyl radical;

$R_1$ and $R_2$ independently denote an alkyl group having from 1 to 22 carbon atoms, a hydroxyalkyl group in which the alkyl group has from 1 to 5 carbon atoms, a lower amido alkyl group in which the alkyl group has from 1 to 5 carbon atoms, or $R_1$ and $R_2$ can denote, together with the nitrogen atom to which they are attached, a heterocyclic group; and $Y^-$ is an anion; and (C) at least one additional ingredient chosen from ethylene glycol monostearate, ethylene glycol distearate, distearyl ether, and 1-hexadecyloxyoctadodecanol, optionally leaving the composition on the keratin substance for a period of time, and then rinsing said keratin substance with water.

* * * * *

UNITED STATES PATENT AND TRADEMARK OFFICE
CERTIFICATE OF CORRECTION

PATENT NO.    : 6,417,145 B1
DATED         : July 9, 2002
INVENTOR(S)   : Decoster et al.

It is certified that error appears in the above-identified patent and that said Letters Patent is hereby corrected as shown below:

Column 13,
Line 64, "diallyidimethylammonium" should read -- diallyldimethylammonium --.

Column 15,
Line 12, "prowess" should read -- process --.

Column 16,
Line 46, "diallyidimethylammonium" should read -- diallyldimethylammonium --.

Signed and Sealed this

Tenth Day of December, 2002

JAMES E. ROGAN
*Director of the United States Patent and Trademark Office*